United States Patent
Kojima et al.

(10) Patent No.: US 9,005,227 B2
(45) Date of Patent: Apr. 14, 2015

(54) FLUID EJECTION DEVICE AND METHOD OF CONTROLLING FLUID EJECTION DEVICE

(75) Inventors: Hideki Kojima, Matsumoto (JP); Shigeo Sugimura, Okaya (JP); Kunio Tabata, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 609 days.

(21) Appl. No.: 12/868,472

(22) Filed: Aug. 25, 2010

(65) Prior Publication Data
US 2011/0054505 A1    Mar. 3, 2011

(30) Foreign Application Priority Data

Aug. 26, 2009 (JP) ................ 2009-195122
Mar. 25, 2010 (JP) ................ 2010-071012

(51) Int. Cl.
*A61B 17/3203* (2006.01)
*B41J 2/14* (2006.01)

(52) U.S. Cl.
CPC ......... *B41J 2/14104* (2013.01); *A61B 17/3203* (2013.01); *B41J 2/14274* (2013.01)

(58) Field of Classification Search
USPC ............ 606/107, 159, 167, 170; 604/131, 21, 604/48, 44; 83/53, 177
See application file for complete search history.

(56) References Cited

U.S. PATENT DOCUMENTS

| | | | |
|---|---|---|---|
| 5,261,883 A * | 11/1993 | Hood et al. .................... | 604/153 |
| 5,491,499 A | 2/1996 | Bibbe | |
| 5,674,226 A | 10/1997 | Doherty | |
| 2003/0105422 A1 | 6/2003 | Gonon | |
| 2007/0073309 A1 * | 3/2007 | Kadziauskas et al. ........ | 606/107 |
| 2008/0086077 A1 | 4/2008 | Seto et al. | |
| 2009/0043480 A1 | 2/2009 | Seto et al. | |

FOREIGN PATENT DOCUMENTS

| | | |
|---|---|---|
| DE | 10133765 | 1/2003 |
| JP | 63-099853 | 5/1988 |
| JP | 2008-082202 | 4/2008 |
| JP | 2009-039384 | 2/2009 |

OTHER PUBLICATIONS

ERBE USA Incorporated Surgical Systems, ERBEJET 2 Water-jet precision for tissue selective dissection, http://www.erbe-usa.com/products/, ERBE USA, Marietta, Georgia. Retrieved Sep. 27, 2011.

* cited by examiner

*Primary Examiner* — Ryan Severson
*Assistant Examiner* — Rachel S Papeika
(74) *Attorney, Agent, or Firm* — Maschoff Brennan

(57) ABSTRACT

A fluid ejection device includes: a fluid chamber; a volume varying unit configured to vary the volume of the fluid chamber; a fluid supplying unit configured to supply fluid to the fluid chamber at a predetermined pressure; and an ejection command switching unit configured to switch a fluid ejection between a pulsed flow ejection which ejects the fluid in a pulsed manner by activating the volume varying unit and varying the volume of the fluid chamber and a continuous flow ejection which ejects the fluid with a fluid supply pressure from the fluid supplying unit higher than that in the case of the pulsed flow ejection in a state in which the volume varying unit is stopped.

5 Claims, 3 Drawing Sheets

FLUID EJECTION DEVICE AND METHOD OF CONTROLLING FLUID EJECTION DEVICE

This application claims priority to Japanese Patent Application No. 2009-195122, filed on Aug. 26, 2009, and to Japanese Patent Application No. 2010-071012, filed on Mar. 25, 2010, the entirety of which are hereby incorporated by reference.

BACKGROUND

1. Technical Field

The present invention relates to a fluid ejection device which allows switching operation between a pulsed flow ejection and a continuous flow ejection, and a method of controlling the fluid ejection device.

2. Related Art

In the related art, there are surgical instruments configured to supply liquid from a pump into a tube introduced into a body cavity at a high pressure, eject the liquid from a nozzle at a distal end of the tube, and excise tissue in the body cavity by a fluid pressure (for example, see JP-A-63-99853).

There is also proposed fluid ejection devices configured to vary the volume of a fluid chamber abruptly by a volume varying unit, transform fluid into a pulsed flow to cause the same to be ejected from a nozzle at a high speed in a pulsed manner, and excise or incise living tissue by an impact pressure thereof (see JP-A-2008-82202).

In JP-A-63-99853, since a high-pressure liquid is introduced to the nozzle via the tube having flexibility, even if the pulsed flow is generated by the pump, the liquid is ejected as the continuous flow. When performing incision of living tissue by the continuous flow ejection, the incision is performed so as to open up an operative site by the fluid pressure. Therefore, it is necessary to increase a liquid supply pressure in order to achieve a sufficient incision performance.

According to JP-A-2008-82202, the fluid is transformed into the pulsed flow by the volume varying unit to eject the pulsed flow from the nozzle. In this case, since the incision and excision are performed so as to scrape off living tissue by the impact pressure of a bow wave or fluid particles of the pulsed fluid, a fluid supply pressure may be low, and the quantity of liquid supply may be small as well.

As described above, since the excision performance or excision characteristics with respect to living tissue are different between the continuous flow ejection and the pulsed flow ejection, it is preferable to selectively use the continuous flow and the pulsed flow according to the operative site or the excision characteristics.

Accordingly, selectively using two types of fluid ejection devices for the continuous flow ejection and the pulsed flow ejection is conceivable. However, it is troublesome to selectively use the fluid ejection devices as occasion demands and operability is remarkably lowered.

In the case of the fluid ejection device according to JP-A-2008-82202, when drive of the volume varying unit is stopped, the continuous flow ejection is enabled. However, in this state, a sufficient fluid supply pressure is not obtained and hence the excision performance is lowered. In particular, with a configuration to realize a high-pressure pulsed flow by an inertance effect of the fluid without the provision of a check valve as in the case of JP-A-2008-82202, a conduit is set to have a very small cross-sectional area or to be very long in order to increase the inertance at a part of the flow channel. Therefore, the flow channel resistance is increased, and the ejection at a required pressure can hardly be obtained by the continuous flow ejection even though the drive of the volume varying unit is simply switched.

SUMMARY

An advantage of some aspects of the invention is to solve at least a part of the problems mentioned above and the invention can be implemented as the following embodiments or application examples.

Application Example 1

Application Example 1 is directed to a fluid ejection device including: a fluid chamber; a volume varying unit configured to vary the volume of the fluid chamber; a fluid supplying unit configured to supply fluid to the fluid chamber at a predetermined pressure; and an ejection command switching unit configured to switch a fluid ejection between a pulsed flow ejection which ejects the fluid in a pulsed manner by activating the volume varying unit and varying the volume of the fluid chamber and a continuous flow ejection which ejects the fluid with a fluid supply pressure from the fluid supplying unit higher than that in the case of the pulsed flow ejection in a state in which the volume varying unit is stopped.

Application Example 2

Application Example 2 is directed to the fluid ejection device, wherein a cross-sectional area A of a fluid ejection opening from which the fluid is ejected has a relationship: $2.5\pi \times 10^{-9}$ $(m^2) \leq A \leq 22.5\pi \times 10^{-9}$ $(m^2)$, where A $(m^2)$ is the cross-sectional area of the fluid ejection opening, and the ejection command switching unit increases fluid supply pressure to a value which provides a flow rate of the fluid supplied from the fluid supplying unit of at least 20A $(m^3/sec.)$ when performing the continuous flow ejection.

Application Example 3

Application Example 3 is directed to a method of controlling a fluid ejection device including: supplying fluid to a fluid chamber; and switching a fluid ejection between a pulsed flow ejection which ejects the fluid in a pulsed manner by varying the volume of the fluid chamber and a continuous flow ejection which ejects the fluid while maintaining the volume of the fluid chamber, wherein the switching includes performing the continuous flow ejection with a pressure of the fluid to be supplied to the fluid chamber higher than that in the case of the pulsed flow ejection.

According to the configuration and the method of controlling of the fluid ejection device in the Application Examples described above, the single fluid ejection device may be used both for the pulsed flow ejection and the continuous flow ejection by switching the fluid ejection therebetween with the ejection command switching unit. Therefore, the operator is allowed to proceed the surgical operation while switching the fluid ejection between the continuous flow ejection and the pulsed flow ejection easily according to the excision characteristics even during the operation.

Therefore, in the case of the pulsed flow ejection, a high excision performance is obtained at a low flow rate (low pressure), and the surgical operation without being impaired in visibility of the operative site is achieved.

Also, in the case of the continuous flow ejection, the excision performance is enhanced and the operation adequate to the continuous flow ejection such as separation of living tissue is achieved by increasing the fluid supply pressure.

In the case of the continuous flow ejection, the cross-sectional area A of the fluid ejection opening is set to have a relationship: $2.5\pi \times 10^{-9}$ (m²)$\leq A \leq 22.5\pi \times 10^{-9}$ (m²), and the fluid supply pressure is increased to a value which provides a flow rate of 20A (m³/sec.). Therefore, the flow rate of the continuous flow ejected from the circular fluid ejection opening having a diameter of 0.1 to 0.3 mm becomes 20 (m/sec.) or higher. Accordingly, since the continuous flow to be ejected has a sufficient performance to incise or excise living tissue, the operation adequate to the continuous flow ejection such as the separation of living tissue is achieved. Also, operations adequate to fine incision, excision, or separation of living tissue, or to excision of a portion around a blood vessel having a similar thickness are achieved.

BRIEF DESCRIPTION OF THE DRAWINGS

The invention will be described with reference to the accompanying drawings wherein like numbers reference like elements.

DESCRIPTION OF EXEMPLARY EMBODIMENTS

Figure 1:
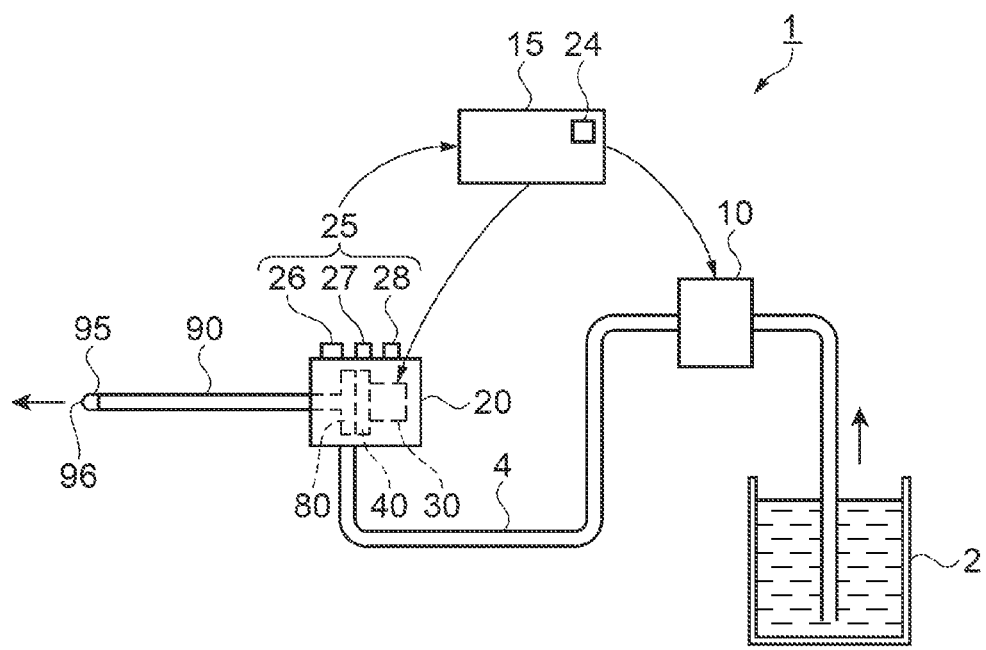
FIG. 1 is an explanatory configuration drawing showing a fluid ejection device as a surgical instrument according to a first embodiment.

Referring now to the drawings, an embodiment of the invention will be described.

A fluid ejection device according to an embodiment of the invention may be employed in various applications such as drawing using ink or the like, washing of precise substances or structures, surgical knives, and so on. The fluid ejection device adequate to incising or excising living tissue is exemplified for description below. Therefore, the fluid used in the embodiment is liquid such as water or physiologic saline.

First Embodiment

FIG. 1 is an explanatory configuration drawing showing a fluid ejection device as a surgical instrument according to a first embodiment. In FIG. 1, a fluid ejection device 1 includes a fluid supply container 2 in which fluid is stored, a pump 10 as a fluid supplying unit, a pulsed flow generator 20 configured to transform fluid supplied from the pump 10 into a pulsed flow (hereinafter, it may be referred to as "pulsed flow"), and a drive control unit 15 configured to control drive of the pump 10 and the pulsed flow generator 20. The pump 10 and the pulsed flow generator 20 are connected by a fluid supply tube 4.

A connecting flow channel tube 90 having a form of a thin pipe is connected to the pulsed flow generator 20. A nozzle 95 having a fluid ejection opening 96 with a reduced flow channel diameter is fixedly inserted to a distal end of the connecting flow channel tube 90. The connecting flow channel tube 90 has rigidity to the extent of not being deformed when the fluid is ejected.

The pulsed flow generator 20 includes a fluid ejection switching unit 25. In this embodiment, a pulsed flow command switch 26 configured to select the pulsed flow ejection as an ejection command switching unit, a continuous flow command switch 27 configured to select the continuous flow ejection, and an OFF switch 28 configured to stop the fluid ejection are provided.

The flow of fluid in the fluid ejection device 1 configured in this manner will be described briefly. The fluid stored in the fluid supply container 2 is sucked by the pump 10 and is supplied to the pulsed flow generator 20 via the fluid supply tube 4 at a constant pressure. The pulsed flow generator 20 is provided with a fluid chamber 80 (see FIG. 2), and a piezoelectric element 30 and a diaphragm 40 as volume varying units configured to vary the volume of the fluid chamber 80. The pulsed flow generator 20 drives the piezoelectric element 30 to generate a pulsed flow in the fluid chamber 80, and ejects the fluid at a high speed in the pulsed manner from the fluid ejection opening 96 via the connecting flow channel tube 90 and the nozzle 95.

When the pulsed flow generator 20 stops driving, the fluid supplied from the pump 10 passes through the fluid chamber 80, and then is ejected as a continuous flow from the fluid ejection opening 96.

The pulsed flow here means a fluid flow flowing in the constant direction and being associated with periodic or non-periodic variations in flow rate or flow velocity of the fluid. The pulsed flow includes an intermittent flow in which flow and stop of the fluid are repeated, but does not necessarily have to be the intermittent flow because what is essential is that the flow rate or the flow velocity of the fluid is varied periodically or nonperiodically.

In the same manner, ejecting the fluid in the pulsed manner means an ejection of fluid in which the flow rate or the moving velocity of the fluid to be ejected varies periodically or nonperiodically. As an example of the ejection in the pulsed manner, an intermittent ejection in which ejection and non-ejection of the fluid are repeated is exemplified. However, it does not necessarily have to be the intermittent ejection as long as the flow rate or the moving velocity of the fluid to be ejected varies periodically or nonperiodically.

Subsequently, a configuration of the pulsed flow generator 20 according to this embodiment will be described.

Figure 2:
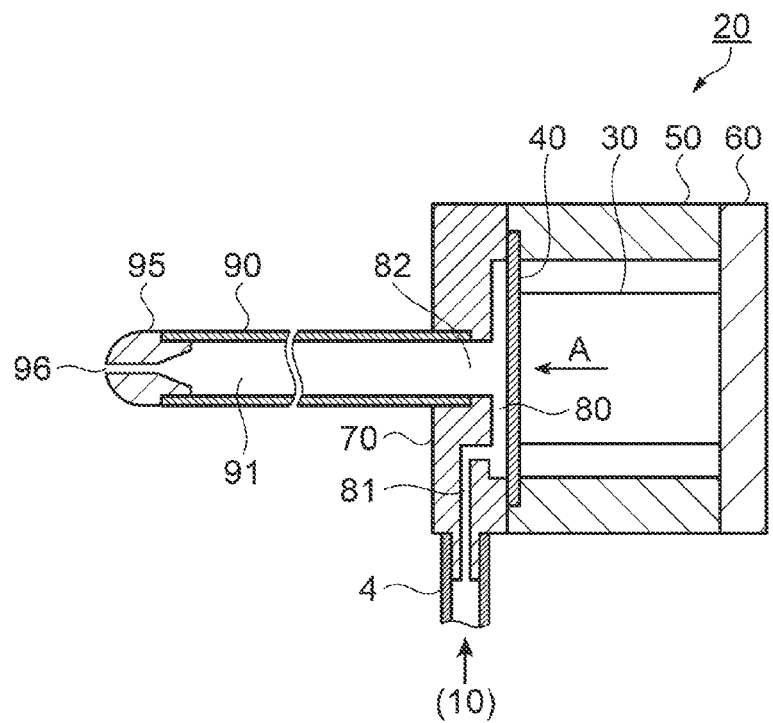
FIG. 2 is a cross-sectional view showing a cross section of a pulsed flow generator taken along the direction of fluid ejection according to the first embodiment.

FIG. 2 is a cross-sectional view showing a cross section of the pulsed flow generator taken along the direction of fluid ejection according to the first embodiment. FIG. 2 is a schematic drawing in which vertical and lateral reduction scales of members or portions are different from reality for the sake of convenience. The pulsed flow generator 20 includes an inlet flow channel 81 for supplying the fluid from the pump 10 into the fluid chamber 80 via the fluid supply tube 4, the piezoelectric element 30 and the diaphragm 40 as the volume varying units for varying the volume in the fluid chamber 80, and an outlet flow channel 82 being in communication with the fluid chamber 80. The fluid supply tube 4 is connected to the inlet flow channel 81.

The diaphragm 40 is formed of a disk-shaped metallic thin plate. The diaphragm 40 is in tight contact between a case 50 and a case 70. The piezoelectric element 30 exemplified in this embodiment is a stacked piezoelectric element, and one of the both ends of the stacked piezoelectric element is secured to the diaphragm 40 and the other end is secured to a bottom plate 60.

The fluid chamber 80 is a space defined by a depression formed on a surface of the case 70 opposing the diaphragm 40 and the diaphragm 40. The fluid chamber 80 includes the outlet flow channel 82 opened at a substantially center portion thereof.

The case 70 and the case 50 are integrally joined at respective surfaces opposing to each other. The connecting flow channel tube 90 having a connecting flow channel 91 which communicates with the outlet flow channel 82 is fixedly fitted to the case 70, and the nozzle 95 is fixedly inserted to the distal end of the connecting flow channel tube 90. The nozzle 95 includes the fluid ejection opening 96 with a reduced flow channel diameter opened therethrough.

Subsequently, a configuration of a drive control unit according to this embodiment will be described.

Figure 3:
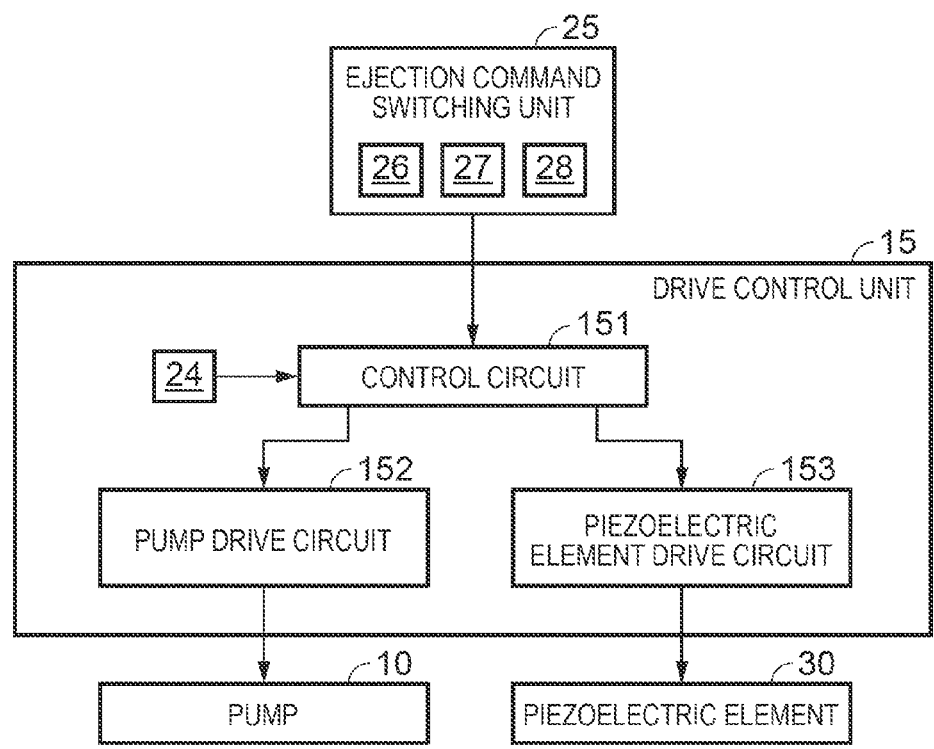
FIG. 3 is an explanatory block diagram showing a schematic configuration of a drive control unit according to the first embodiment.

FIG. 3 is an explanatory block diagram showing a schematic configuration of the drive control unit of this embodiment. The drive control unit 15 includes a pump drive circuit 152 configured to control drive of the pump 10, a piezoelectric element drive circuit 153 configured to control drive of the piezoelectric element 30, a control circuit 151 configured to control the pump drive circuit 152 and the piezoelectric element drive circuit 153, and a main switch 24.

The control circuit 151 includes programs which sets a drive frequency of the pump 10 which determines the fluid supply flow rate (that is, supplied pressure) from the pump 10, the amount of the volume variations of the fluid chamber 80 which determines an incision power per pulse (displacement volume), and a frequency of the volume variation of the fluid chamber 80 which determines the excision speed (which corresponds to the drive frequency of the piezoelectric element 30) stored therein.

Subsequently, functions of the respective switches will be described. The main switch 24 has a function to activate and stop the fluid ejection device 1 and, more specifically, turns the control circuit 151 ON (activation) and OFF (stop).

The pulsed flow command switch 26 drives the pump 10 at a low pressure and activates the pulsed flow generator 20. The continuous flow command switch 27 drives the pump 10 at a high pressure and stops the pulsed flow generator 20. Switching of the fluid ejection from the pulsed flow ejection to the continuous flow ejection during the drive of the fluid ejection device 1 is achieved by operating (turning ON) the continuous flow command switch 27. Switching of the fluid ejection from the continuous flow ejection to the pulsed flow ejection is achieved by operating (turning OFF) the pulsed flow command switch 26. Stopping the ejection is achieved by operating the OFF switch 28.

Referring now to FIG. 1 and FIG. 2, a pulsed flow ejecting operation of the pulsed flow generator 20 in this embodiment will be described. Fluid discharge of the pulsed flow generator 20 in this embodiment is achieved by the difference between a composite inertance L1 on the side of the inlet flow channel 81 and a composite inertance L2 on the side of the outlet flow channel 82.

First of all, inertance will be described.

An inertance L is expressed by $L = \rho \times h / S$, where $\rho$ is the density of the fluid, S is the cross-sectional area of the flow channel, and h is the length of the flow channel. A relationship: $\Delta P = L \times dQ/dt$ is delivered by deforming a dynamic equation in the flow channel using the inertance L, where $\Delta P$ is the pressure difference in the flow channel, Q is the flow rate of the fluid flowing in the flow channel.

In other words, the inertance L indicates the degree of influence affected on variations of flow rate with time. The larger the value of the inertance L, the smaller the variations of flow rate with time becomes. The smaller the value of the inertance L, the larger the variations of flow rate with time becomes.

The composite inertance L1 on the side of the inlet flow channel 81 is calculated within a range of the inlet flow channel 81. Since the fluid supply tube 4 which connects the pump 10 and the inlet flow channel 81 has flexibility, it may be excluded from the calculation of the composite inertance L1.

The composite inertance L2 on the side of the outlet flow channel 82 is an inertance within a range of the outlet flow channel 82 and the connecting flow channel 91 in this embodiment. The thickness of a tube wall of the connecting flow channel tube 90 provides sufficient rigidity with respect to pressure propagation of the fluid.

In this embodiment, the length and the cross-sectional area of the inlet flow channel 81 and the length and the cross-sectional area of the outlet flow channel 82 are designed to make the composite inertance L1 on the side of the inlet flow channel 81 larger than the inertance L2 on the side of the outlet flow channel 82.

The fluid is supplied to the inlet flow channel 81 at a predetermined pressure by the pump 10. The fluid supply flow rate from the pump 10 needs only to be substantially the same as the quantity of pulsed flow ejection. When the piezoelectric element 30 does not take any action, the fluid is allowed to flow into the fluid chamber 80 because of the difference between a discharge force of the pump 10 and a flow channel resistance of the entire part of the inlet flow channel 81.

Assuming that a drive signal is input to the piezoelectric element 30 and hence the piezoelectric element 30 is abruptly expanded in the direction vertical to a surface of the diaphragm 40 on the side of the fluid chamber 80 (direction of an arrow A), the volume of the fluid chamber 80 is reduced, and the pressure in the fluid chamber 80 rises abruptly and reaches several tens atmospheric pressure if the composite inertances L1, L2 on the side of the inlet flow channel 81 and on the side of the outlet flow channel 82 have enough magnitude.

Since this pressure in the fluid chamber 80 is far higher than the pressure applied to the inlet flow channel 81 by the pump 10, an inflow of the fluid from the inlet flow channel 81 into the fluid chamber 80 is reduced by the pressure applied thereto and an outflow of the fluid from the outlet flow channel 82 is increased.

Since the composite inertance L1 on the side of the inlet flow channel 81 is larger than the composite inertance L2 on the side of the outlet flow channel 82, the amount of increase in fluid to be ejected from the outlet flow channel 82 is larger than the amount of decrease in flow rate flowing from the inlet flow channel 81 into the fluid chamber 80. Consequently, pulsed liquid discharge, that is, the pulsed flow is generated in the connecting flow channel 91. Pressure variations at the time of this discharge propagate in the interior of the connecting flow channel tube 90 (the connecting flow channel 91), and the fluid is ejected from the fluid ejection opening 96 of the nozzle 95 at the distal end.

As the flow channel diameter of the fluid ejection opening 96 is reduced from the flow channel diameter of the outlet flow channel 82, the fluid is subjected to a higher pressure, and hence is ejected at a high speed in the form of pulsed liquid droplets.

In contrast, the interior of the fluid chamber 80 is brought into a low-pressure state (almost vacuumed state) immediately after the pressure rise because of the mutual action of the reduction in amount of the fluid flowing from the inlet flow channel 81 and the increase in amount of the fluid flowing out from the outlet flow channel 82. When the piezoelectric element 30 is restored to its original shape, the flow of the fluid in the inlet flow channel 81 proceeding to the interior of the fluid chamber 80 at the same speed as that before action (before expansion) of the piezoelectric element 30 is recovered after elapse of a certain time because of both the pressure of the pump 10 and the low pressure state in the fluid chamber 80.

If the piezoelectric element 30 is expanded again after the flow of the fluid in the inlet flow channel 81 is restored, the pulsed liquid droplets are ejected continuously from the fluid ejection opening 96.

When the drive of the pulsed flow generator 20 is stopped while continuing the supply of the fluid from the pump 10 at a predetermined pressure, the fluid passes through the inlet flow channel 81, the fluid chamber 80, and the outlet flow channel 82, and then reaches the fluid ejection opening 96. At this time, since the piezoelectric element 30 is stopped, the fluid is ejected from the fluid ejection opening 96 as a continuous flow. Since the diameter of the flow channel of the fluid ejection opening 96 is reduced by far from the diameters of the flow channels of the outlet flow channel 82 and the connecting flow channel 91, the fluid is ejected at a high speed at a higher pressure than the supplied pressure from the pump 10.

Figures 4A, 4B:
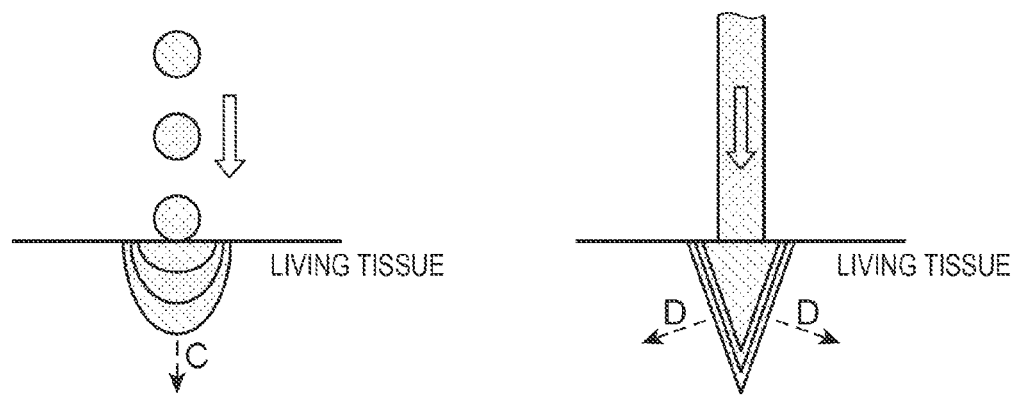
FIG. 4A is a schematic explanatory drawing showing excision characteristics of a pulsed flow ejection.
FIG. 4B is a schematic explanatory drawing showing excision characteristics of a continuous flow ejection.

Subsequently, excision characteristics of the continuous flow ejection and the pulsed flow ejection will be described. FIG. 4A is a schematic explanatory drawing showing the excision characteristics of the pulsed-flow ejection. FIG. 4B is a schematic explanatory drawing showing the excision characteristics of the continuous flow ejection. In the case of the pulsed flow ejection, the excision is performed so as to scrape off living tissue mainly by the impact pressure of the bow wave or fluid particles of the pulsed fluid (shown by an arrow indicated by C in the drawing). In this case, the factors which determine an excision power by the impact pressure of one pulse are the amount of volume variation (displacement volume) of the fluid chamber 80 which determines the size of the fluid particles of the pulsed flow, and the speed of reduction of the volume of the fluid chamber 80 which determines the speed of the fluid particles of the pulsed flow (which corresponds to the drive time of the piezoelectric element 30 when reducing the volume of the fluid chamber 80). Therefore, the fluid supply pressure may be low.

In the case of the continuous flow ejection, the excision (incision) is performed while opening up living tissue with the fluid pressure of the fluid ejected continuously (indicated by an arrow D in the drawing). Therefore, the excision power by the fluid pressure is affected by the fluid supply pressure applied by the pump 10. In other words, in order to increase the excision power by the fluid pressure to a level equal to or higher than the excision power on the basis of the impact pressure, the fluid supply pressure of the pump 10 must be increased to a level higher than that in the case of the pulsed flow ejection.

As described above, various objects of surgical operation are supported by selectively using the excision characteristics of the pulsed flow ejection and the continuous flow ejection.

Figure 5:
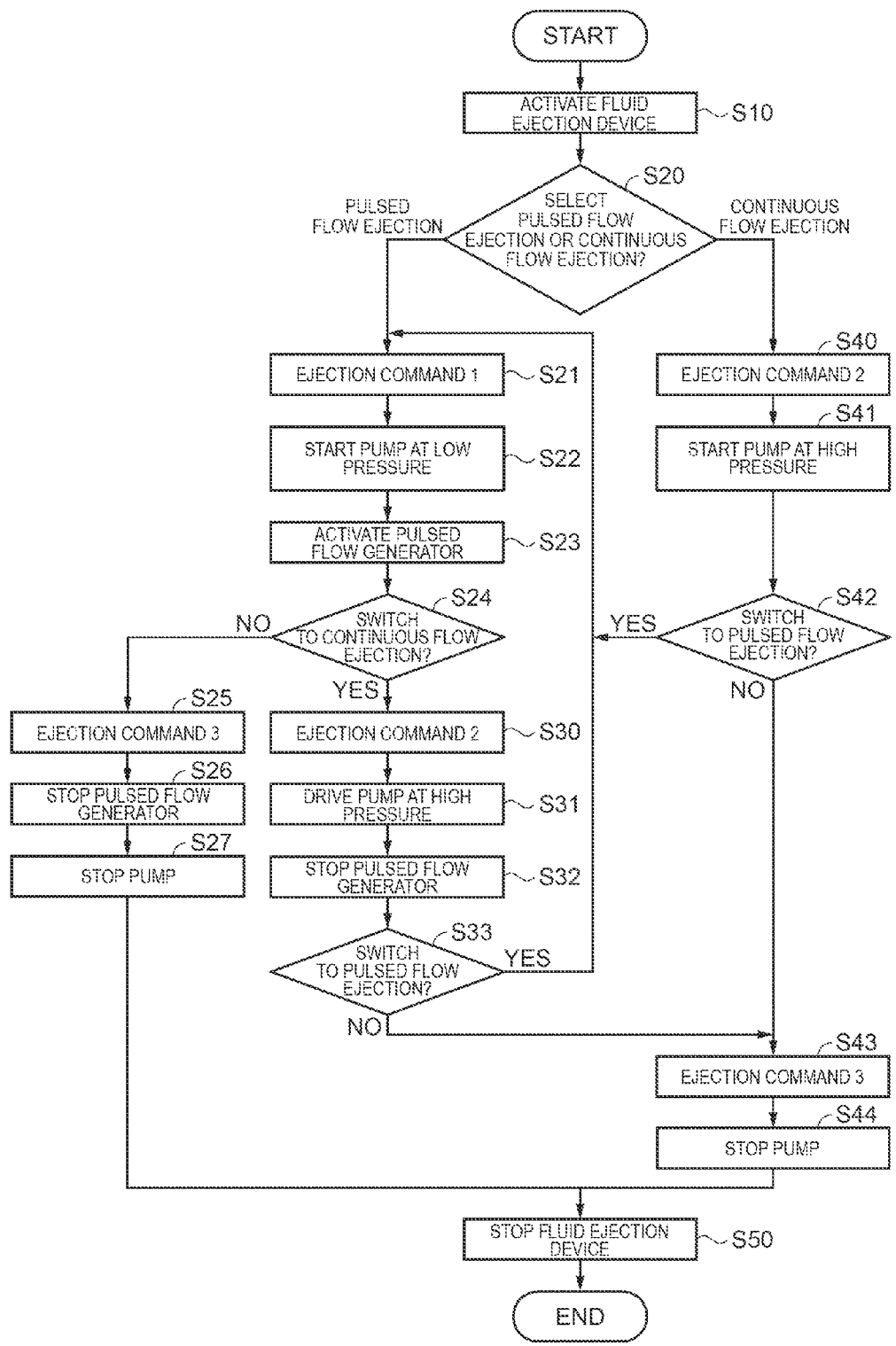
FIG. 5 is an explanatory flowchart showing a method of controlling the fluid ejection device.

Subsequently, a method of controlling the fluid ejection when using a single piece of the fluid ejection device 1 by switching the fluid ejection between the pulsed flow ejection and the continuous flow ejection will be described.
Method of Controlling Fluid Ejection Device FIG. 5 is an explanatory flowchart showing the method of controlling the fluid ejection device. FIGS. 1 to 3 are also referenced. Table 1 shows the functions of the respective switches relating to the control commands.

TABLE 1

| Ejection Command Switching Unit | Pulsed Flow Command Switch 26 | Continuous Flow Command Switch 27 | OFF Switch 28 |
|---|---|---|---|
| Ejection Command Function | Ejection Command 1 Ejection of Pulsed Flow | Ejection Command 2 Ejection of Continuous Flow | Ejection Command 3 Stop Ejection |

First of all, the main switch 24 is operated to activate the fluid ejection device 1 (S10). In other words, the control circuit 151 is activated. Then, either the pulsed flow ejection or the continuous flow ejection is selected (S20).

In order to select the pulsed flow ejection, the pulsed flow command switch 26 is operated to input Ejection Command 1 to the control circuit 151 (S21). In order to select the continuous flow ejection, the continuous flow command switch 27 is operated to input Ejection Command 2 to the control circuit 151 (S40).

First of all, the case of the pulsed flow ejection will be described. Upon input of Ejection Command 1, a drive command is input from the control circuit 151 to the pump drive circuit 152, and the pump 10 starts low-pressure drive (S22). Then, fluid supply to the pulsed flow generator 20 is started at a constant pressure. Subsequently, the drive command is input from the control circuit 151 to the piezoelectric element drive circuit 153 and hence the pulsed flow generator 20 (specifically, the piezoelectric element 30) is activated (S23), thereby starting the pulsed flow ejection.

If switching to the continuous flow ejection is wanted after having continued the pulsed flow ejection, the procedure goes to the next step. Then, whether or not to switch to the continuous flow ejection is determined (S24). If it is determined not to switch the fluid ejection to the continuous flow ejection, the pulsed flow ejection is continued. In order to stop the ejection thereafter, the OFF switch 28 is operated to input Ejection Command 3 to the control circuit 151 (S25). A stop command is input from the control circuit 151 to the piezoelectric element drive circuit 153 upon issuing of Ejection Command 3, and hence drive of the pulsed flow generator 20 (that is, the piezoelectric element 30) is stopped (S26). Then, the stop command is input from the control circuit 151 to the pump drive circuit 152 to stop the drive of the pump (S27), thereby ending the fluid ejection operation. Subsequently, the main switch 24 is operated to stop the entire system of the fluid ejection device 1 (S50).

In order to switch the fluid ejection from the pulsed flow ejection to the continuous flow ejection, the continuous flow command switch 27 is operated to input Ejection Command 2 to the control circuit 151 (S30). Upon input of Ejection Command 2, a command to drive the pump 10 at a higher fluid supply pressure than the case of the pulsed flow ejection is input from the control circuit 151 to the pump drive circuit 152, so that the pump 10 is driven at a high pressure (S31).

The fluid supply pressure in the case of the continuous flow ejection is set to an adequate pressure in advance according to the objects to be excised or the excision characteristics, and the program therefor is stored in the control circuit 151. The drive of the pulsed flow generator 20 is stopped substantially simultaneously with the start of the high-pressure drive of the pump 10 (S32), and the continuous flow ejection is started.

Here, the fluid supply pressure in the case of the continuous flow ejection will be described. In the fluid ejection device for excising living tissue, the ejected continuous flow has a sufficient performance to incise or excise living tissue. Therefore, the flow velocity of the continuous flow ejected from the fluid ejection opening is preferably equal to and more than 20 (m/sec.). Therefore, the sufficient performance to incise or excise living tissue is achieved even with the continuous flow ejection by setting the fluid supply pressure to a value which provides a flow velocity of the continuous flow ejected from the fluid ejection opening of at least 20 (m/sec.) when switching the fluid ejection from the pulsed flow ejection to the continuous flow ejection.

The flow velocity of the fluid in the case of the continuous flow depends on the supplied flow rate and the cross-sectional area of the flow channel. Here, it is assumed that the flow rate supplied from the fluid supplying unit is Q ($m^3$/sec.), the flow velocity of the fluid ejected from the fluid ejection opening is V (m/sec.), and the cross-sectional area of the fluid ejection opening is A ($m^2$). In the fluid ejection device for excising living tissue, it is recommended to set the diameter of the fluid ejection opening of the fluid ejection nozzle to approximately 0.1 mm to 0.3 mm in order to perform operations adequate to fine incision, excision, or separation, or to excision of a portion around a blood vessel having a similar thickness. Therefore, the cross-sectional area A of the fluid ejection opening is preferably $2.5\pi \times 10^{-9}$ $m^2$ to $22.5\pi \times 10^{-8}$ $m^2$.

At this time, the flow velocity V of the fluid ejected from the fluid ejection opening is expressed by the following expression: V=Q/A.

If the flow velocity V of the fluid ejected from the fluid ejection opening is not lower than 20 (m/sec.), a sufficient performance to incise or excise living tissue is obtained. Therefore, the condition of the flow rate Q supplied from the fluid supply unit for enabling incision or excision of living tissue with the continuous flow ejection has inequality as: Q≥20A.

Therefore, the continuous flow ejection is provided with the performance to incise or excise living tissue by increasing the fluid supply pressure to a value which provides a flow rate supplied from the fluid supply unit of at least 20A ($m^3$/sec.). Since the fluid supply pressure and the flow rate supplied from the fluid supplying unit has a mutual relationship, the flow rate supplied from the fluid supplying unit increases as the fluid supply pressure increases.

For example, in this embodiment, assuming that the cross-sectional area of the fluid ejection opening 96 is $1 \times 10^{-8}$ ($m^2$), 20 (m/sec.) or higher flow velocity is obtained for the continuous flow ejected from the fluid ejection opening 96 by increasing the fluid supply pressure of the pump 10 to a value which provides a quantity of fluid supply of $20 \times 10^{-8}$ ($m^2$/sec.) or higher in the case of the continuous flow ejection.

The upper limit of the pressure of the pump 10 in the case of the continuous flow ejection may be determined according to the performance of the pump 10 or on the basis of the resistance to pressure of components used in the fluid ejection device (for example, the resistance to pressure of the fluid supply tube 4).

When switching back to the pulsed flow ejection again is wanted after having continued the continuous flow ejection, whether or not to switch the fluid ejection to the pulsed flow ejection is determined (S33). If it is determined not to transfer to the pulsed flow ejection, the continuous flow ejection is continued as is, and when stopping the ejection thereafter, the OFF switch 28 is operated to input Ejection Command 3 to the control circuit 151 (S43). Upon input of Ejection Command 3, a pump stop command is input from the control circuit 151 to the pump drive circuit 152. Then, the pump 10 is stopped (S44) and the fluid ejection is ended. Subsequently, the main switch 24 is operated to stop the entire system of the fluid ejection device 1 (S50).

In order to switch the fluid ejection from the continuous flow ejection to the pulsed flow ejection in Step 33 (S33) again, the pulsed flow command switch 26 is operated to input Ejection Command 1 to the control circuit 151 (S21). The pump 10 is switched to the low-pressure drive by Ejection Command 1 (S22), and then the pulsed flow generator 20 (that is, the piezoelectric element 30) is activated (S23) to transfer the ejection to the pulsed flow ejection. Thereafter, either the continuous flow ejection or the pulsed flow ejection is selected according to a control step from Step 24 (S24) onward.

Subsequently, a method of controlling the fluid ejection when causing the fluid ejection device 1 to perform the continuous flow ejection after having activated the fluid ejection device 1 (S10) will be described. After having activated the fluid ejection device 1, the continuous flow ejection is selected (S20). Subsequently, the continuous flow command switch 27 is operated to input Ejection Command 2 to the control circuit 151 (S40). Upon input of Ejection Command 2, a command to drive the pump 10 at a higher fluid supply pressure is input from the control circuit 151 to the pump drive circuit 152, so that the pump 10 is driven at a high pressure (S41). Here, the fluid supply pressure from the pump 10 in the case of the continuous flow ejection is set to be higher than the supply pressure in the case of the pulsed flow ejection.

After having continued the continuous flow ejection, whether or not to switch the fluid ejection to the pulsed flow ejection is determined (S42). If it is determined not to transfer to the pulsed flow ejection, the continuous flow ejection is continued as is, and when stopping the ejection thereafter, the OFF switch 28 is operated to input Ejection Command 3 to the control circuit 151 (S43). Upon input of Ejection Command 3, the pump stop command is input from the control circuit 151 to the pump drive circuit 152. Then, the pump 10 is stopped (S44) and the fluid ejection is ended. Then, the main switch 24 is operated to stop the entire system of the fluid ejection device 1 (S50).

In order to switch the fluid ejection from the continuous flow ejection to the pulsed flow ejection in Step 42 (S42), the pulsed flow command switch 26 is operated to input Ejection Command 1 to the control circuit 151 (S21). The pump 10 is switched to the low-pressure drive by Ejection Command 1 (S22), and then the pulsed flow generator 20 (that is, the piezoelectric element 30) is activated (S23) to transfer the ejection to the pulsed flow ejection. Thereafter, either the continuous flow ejection or the pulsed flow ejection is selected according to the control step from Step 24 (S24) onward.

According to the configuration and the method of controlling the fluid ejection device described above, the single fluid ejection device may be used both for the pulsed flow ejection and the continuous flow ejection by switching the fluid ejection therebetween with the ejection command switching unit 25. Therefore, the operator is allowed to proceed the surgical operation while switching the fluid ejection between the continuous flow ejection and the pulsed flow ejection easily according to the excision characteristics even during the operation.

In the case of the pulsed flow ejection, the ejection is performed so as to scrape off living tissue mainly by the impact pressure of the bow wave or fluid particles of the pulsed fluid. Therefore, the factors which determine the excision power by the impact pressure of one pulse are the amount of volume variation (displacement volume) of the fluid chamber 80 which determines the size of the fluid particles of the pulsed flow, and a speed of reducing the volume of the fluid chamber 80 which determines the speed of the fluid particles of the pulsed flow (which corresponds to the drive time of the piezoelectric element 30 when reducing the volume of the fluid chamber 80). Therefore, the fluid supply pressure may be low.

For example, in this embodiment, it is assumed that the cross-sectional area of the fluid ejection opening 96 is $1\times10^{-8}$ (m$^2$) as exemplified before. At this time, if the fluid ejection is the pulsed flow ejection, the incision or excision of living tissue is achieved even when the fluid supply pressure of the pump 10 which provides a fluid supply flow rate from the pump 10 is set to less than $20\times10^{-8}$ (m$^3$/sec.)

Therefore, in the case of the pulsed flow ejection, a high excision performance is obtained at a low flow rate (low pressure), and the surgical operation without being impaired in visibility of operative site is achieved.

In the case of the continuous flow ejection, the excision (incision) is performed while opening up living tissue with the fluid pressure of the fluid ejected continuously. Therefore, the excision power by the fluid pressure is affected by the fluid supply pressure applied by the pump 10. In other words, in order to achieve the excision power on the basis of the fluid pressure equal to or higher than the excision power on the basis of the impact pressure, it is necessary to increase the fluid supply pressure of the pump 10 to be higher than that in the case of the pulsed flow ejection. In particular, it is effective in the configuration in which the high-pressure pulsed flow is achieved by the inertance effect of the fluid without providing a check valve as in JP-A-2008-82202 or in this embodiment.

Therefore, in the case of the continuous flow ejection, the excision performance is enhanced and the operation adequate to the continuous flow ejection such as separation of living tissue is achieved by increasing the fluid supply pressure.

In this manner, various objects of surgical operation are supported by selectively using the incision characteristics of the pulsed flow ejection and the continuous flow ejection.

The operator performs the surgical operation while holding the fluid ejection device 1 in hand. As the ejection command switching unit 25 includes a group of switches provided on the fluid ejection device 1, the operability is excellent because the operator is capable of selecting the pulsed flow ejection or the continuous flow ejection by the operation at hand.

With the provision of specific switches such as the pulsed flow command switch 26, the continuous flow command switch 27, and the OFF switch 28, the operator is capable of controlling the fluid ejection device into the desired state of the fluid ejection by one operation when selecting the pulsed flow ejection, when selecting the continuous flow ejection, and when stopping the ejection, respectively, so that the operability is further enhanced.

In the embodiment described above, switching between the pulsed flow ejection and the continuous flow ejection is achieved by operating the switches. However, a configuration in which the fluid ejection is switched between the pulsed flow ejection and the continuous flow ejection according to the result of detection of a sensor such as a camera provided at a distal end of the nozzle 65 is also applicable.

For example, the excision is performed by the continuous flow ejection while opening up living tissue to allow easy access of the nozzle 65 into a living body until the sensor detects a living tissue to be excised by the image recognition technologies and, when living tissue to be excised is detected, the fluid ejection is switched to the pulsed flow ejection. Accordingly, a manipulation such as performing the excision of living tissue with a small quantity of fluid in the case of malignant tumors or the like, which are susceptible to risks such as metastasis if they are spread out, is achieved without the necessity of operation of the switches by the operator.

Also, in the embodiment, switching between the pulsed flow ejection and the continuous flow ejection is achieved by operating the switches. However, a configuration in which the fluid ejection is switched between the pulsed flow ejection and the continuous flow ejection according to the remaining amount of fluid in the fluid supply container 2 is also applicable. For example, a configuration in which the continuous flow ejection is performed because a large amount of fluid is available when the remaining amount of fluid is larger than a predetermined amount or more, and the pulsed flow ejection which allows excision with a small amount of fluid is performed when the remaining amount of fluid is less than the predetermined amount is also applicable. In particular, as it is difficult to use the fluid limitlessly in regions such as desert where the fluid is precious, the configuration to allow the switching between the pulsed flow ejection and the continuous flow ejection according to the remaining amount of fluid is preferable.

In the embodiment described above, the pulsed flow is generated by pressing the diaphragm 40 by the piezoelectric element 30. However, the invention is not limited thereto, and other modes may be employed as long as the pulsed flow is generated. For example, the pulsed flow may be generated by reducing the volume of the fluid chamber 80 by driving a piston (plunger) using the piezoelectric element. Alternatively, the pulsed flow may be generated by making the liquid in the fluid chamber 80 into foam (bubbles) by laser induction and ejecting the bubbles.

What is claimed is:

1. A tissue removal device which removes tissue by ejecting a fluid at a high speed, the device comprising:
    a fluid chamber;
    a volume varying unit configured to vary the volume of the fluid chamber;
    a fluid supplying unit configured to supply fluid to the fluid chamber; and
    an ejection command switching unit configured to switch a fluid ejection between a pulsed flow ejection which ejects the fluid in a pulsed manner by activating the volume varying unit and a continuous flow ejection which ejects the fluid with a fluid supply pressure from the fluid supplying unit higher than that in the case of the pulsed flow ejection, wherein the volume varying unit is stopped during continuous flow ejection.

2. The tissue removal device according to claim 1, wherein a cross-sectional area A of a fluid ejection opening from which the fluid is ejected has a relationship:

$$2.57\pi\times10^{-9}\,(m^2)\leq A\leq22.5\pi\times10^{-9}\,(m^2),$$

where A (m$^2$) is the cross-sectional area of the fluid ejection opening, and
    the ejection command switching unit increases the fluid supply pressure to a value which provides a flow rate of the fluid supplied from the fluid supplying unit of at least 20A (m/sec)*(m$^3$/sec.) when performing the continuous flow ejection.

3. The tissue removal device according to claim 1, the switching unit being configured to switch between the pulsed flow ejection and the continuous flow ejection according to the remaining amount of the fluid supplying unit.

4. A method of controlling a fluid ejection device comprising:
    supplying fluid to a fluid chamber; and
    switching a fluid ejection between a pulsed flow ejection which ejects the fluid in a pulsed manner by varying a volume of the fluid chamber using a volume varying unit and a continuous flow ejection which ejects the fluid while maintaining the volume of the fluid chamber, wherein the switching includes performing the continuous flow ejection with a pressure of the fluid to be supplied to the fluid chamber higher than that in the case of the pulsed flow ejection, and wherein the volume varying unit is stopped during continuous flow ejection.

5. A tissue removal device which removes tissue by ejecting a fluid, the device comprising:

a fluid chamber;

a bubble generating unit configured to generate bubbles in the fluid chamber;

a fluid supplying unit configured to supply fluid to the fluid chamber; and an ejection command switching unit configured to switch a fluid ejection between a pulsed flow ejection which ejects the fluid in a pulsed manner by activating the bubble generating unit and a continuous flow ejection which ejects the fluid with a fluid supply pressure from the fluid supplying unit which is higher than the fluid supply pressure in the case of pulsed flow ejection, wherein the bubble generating unit stops generating bubbles during continuous flow ejection.

* * * * *